United States Patent [19]

Zoche

[11] Patent Number: 5,391,217
[45] Date of Patent: Feb. 21, 1995

[54] METHOD FOR ELIMINATING MERCURY FROM LIQUIDS

[75] Inventor: Guenter Zoche, Bonn, Germany

[73] Assignee: Huels Aktiengesellschaft, Marl, Germany

[21] Appl. No.: 82,542

[22] Filed: Jun. 28, 1993

[30] Foreign Application Priority Data

Jun. 27, 1992 [DE] Germany ............... 4221207

[51] Int. Cl.⁶ .............................. C22B 3/46
[52] U.S. Cl. ........................ 75/724; 75/742; 210/679; 210/688; 210/914
[58] Field of Search ............ 75/724, 742; 210/679, 210/688, 914

[56] References Cited

U.S. PATENT DOCUMENTS 4,094,777  6/1978  Sugier et al. .............. 210/679
4,230,486 10/1980  Capuano et al. .
4,325,732  4/1982  Woog ....................... 75/724
4,353,741 10/1982  Capuano et al. .

OTHER PUBLICATIONS

Vierspiegelungsvorschriften von z. B. Boettger–Bothe oder Brashear (sieche E. v. Angerer, Techn. Kunstgriffe, 8. Auflage, 1952, S.94 ff).

Primary Examiner—Melvyn J. Andrews
Attorney, Agent, or Firm—Oblon, Spivak, McClelland, Maier & Neustadt

[57] ABSTRACT

A method for eliminating mercury from mercury containing liquids by contacting the mercury-containing liquid with a plurality of fibers wherein the fibers making up the plurality of fibers have a coating of silver on the surface of the fibers, and a silver-coated fiber for use in the method are disclosed.

15 Claims, No Drawings

METHOD FOR ELIMINATING MERCURY FROM LIQUIDS

BACKGROUND OF THE INVENTION

1. Field of the Invention

The present invention relates to a method for eliminating mercury from liquids by amalgam formation with silver and to silver coated fiber for used in the method.

2. Discussion of Background

Due to the high toxicity of mercury, many industrial processes require the elimination of mercury from liquids used in or resulting from the process.

For example, in the production of aqueous alkali metal hydroxides according to the amalgam process, or the preparation of alkali metal alcoholates by reacting alcohols with alkali metal amalgam, solutions are obtained which contain significant levels of mercury. In order to further use these solutions, the mercury must often be eliminated, especially in those cases where the solutions are to be used in food or pharmaceutical applications.

Conventional methods of eliminating mercury from solutions obtained during the preparation of aqueous alkali metal hydroxides primarily involve removal of the mercury by mechanical methods, such as filtration using special carbon filters or centrifuging. While these methods allow the reduction of mercury to a residual level of 0.5 to 1 ppm, this is still insufficient for many applications.

Another conventional process removes mercury from the mercury-contaminated alkali or alcoholate solutions of the above mentioned processes by passing the contaminated solutions over large silver surfaces. During passage over the silver surface, the mercury becomes bound as silver amalgam.

In order to implement the above conventional process in industry, the liquids to be purified flow through pipes or columns which are filled with silver in a suitable form. Obviously, these columns must be highly effective in terms of mercury elimination, and at the same time achieve as high as possible a flow rate per unit time per unit column volume. Thus the mercury elimination efficiency depends on the silver surface area available per unit volume of the column and on the contact time of the liquid with the silver surface.

U.S. Pat. Nos. 4,230,486 and 4,353,741 disclose the use of silver powder, silver granules or silver-coated particles in the above-mentioned types of mercury removal columns. The supports described for the silver include powdered or granular substances made from glass, brick, activated carbons, refractory materials or grinding materials.

However, the efficiency (effectiveness of removal of mercury relative to throughput of liquid being purified) of the mercury elimination using powdered or granular silver materials according to the prior art is significantly limited. While selecting small particles, such as fine powders, does provide a large silver surface area, these same fine powders create extremely high flow resistance to the liquid being purified, such that the flow rate per unit time and unit column volume decreases to the point of making the process uneconomical.

Alternatively, finely porous material, such as activated carbon, has been used as a support for the silver. While activated carbon is known to have a very large internal surface area, it unfortunately offers no advantages in this case since during silvering, the fine porous structures are closed up by silver, making the initially large internal surface area unavailable and ineffective. Thus only the external surface area of the carbon particle, in effect, remains active. Even if small channels remain in the carbon, these become useless because the flow resistance through them is far too large due to capillary forces. A further serious disadvantage to silver-coated activated carbons is their tendency towards explosive decomposition.

Thus a method is needed which provides for removal of mercury from liquids at high levels of effectiveness, while maintaining high levels of throughput of the liquid being purified.

SUMMARY OF THE INVENTION

Accordingly, one object of the present invention is to provide a silver material for eliminating mercury from liquids, which makes it possible to achieve a higher efficiency of mercury elimination compared to the prior art.

Another object of the present invention is to provide a silver-coated fiber capable of eliminating mercury from liquids while maintaining economically high liquid throughputs during purification.

These and other objects of the present invention have been satisfied by the discovery of a method for eliminating mercury from mercury-containing liquids, comprising:

contacting the mercury-containing liquid with a plurality of fibers having a coating of silver on the fiber surface.

DETAILED DESCRIPTION OF THE PREFERRED EMBODIMENTS

The present invention relates to a method for eliminating mercury from a mercury-containing liquid, comprising:

contacting the mercury-containing liquid with a plurality of fibers having a coating of silver.

The invention further relates to the silver-coated fibers used in the above method for eliminating mercury from mercury containing liquids.

The method of the present invention is suitable for eliminating mercury from a large variety of liquids. Suitable liquids include solutions of aqueous alkali metal hydroxides and alkaline earth metal hydroxides, and solutions of alcoholates of alkali metals and alkaline earth metals. Preferred solutions for use in the method of the present invention are solutions of aqueous alkali metal hydroxides and alkali metal alcoholates.

The silver coated fiber of the present invention comprises a fiber which is chemically resistant against the mercury-containing liquid being purified and a silver coating on the surface of the fiber. Suitable fibers include rock wool, slag wool, glass wool, carbon fibers, plastic fibers, such as polyolefins or polystyrene, and metallic fibers such as fibers made from nickel, iron, steel alloys or platinum. Rock wool, slag wool, glass wool, carbon fibers and plastic fibers are preferred, with rock wool, slag wool, glass wool and plastic fibers being most preferred. Polyolefin fibers suitable for the present invention include polyethylene and polypropylene fibers.

While metallic fibers can be used in the present invention, occasionally problems do arise, however, in selecting the appropriate metals or alloys since many metals and alloys are too ductile. Due to this high ductility, when the fibers are in the form of fine fibers, they lack the necessary mechanical stability to be used as a column packing. Additionally, while many other types of metal fibers, such as fibers of nickel, iron, steel alloys and platinum, have the appropriate mechanical stability for use in the present invention, they are either not commercially available or are uneconomically expensive.

The fibers to be coated for use in the method of the present invention can be used either in loose or in processed form. Suitable forms include cloths, felts, bonded fiber webs and mats formed by conventional methods. Tangled webs in pearled form are extremely suitable due to their pourability.

The fibers to be silver-coated preferably have an uncoated diameter of from 5 to 500 $\mu$m, more preferably from 10 to 30 $\mu$m.

The fibers to be coated have a relatively smooth surface. Because of this relatively smooth surface, small silver crystals deposited in isolation do not sufficiently adhere to the fibers and the silver crystals can therefore be detached relatively easily by mechanical forces.

In the method of the present invention, the coating of silver on the fibers may be a complete coating or a partial coating of silver. In the case of a partial coating, it is preferred that the coating be contiguous around the circumference of at least a portion of the fiber in order to maintain the silver coating on the fiber in the event that the silver coating becomes detached from the fiber surface.

According to the present invention it is therefore advantageous to coat the fibers with a circumferentially contiguous silver layer covering more than 10% of the fiber surface, preferably more than 75% of the fiber surface, more preferably 100% of the fiber surface. Thus, even if the silver layer loses adhesion to the fiber, the tubular nature of the silver layer will allow the silver layer to remain on the fiber, much like a plastic sheath on a conventional electrical wire.

If the coating of silver is a partial coating, a higher amount of the coated fiber is required in order to remove a given amount of mercury. For example, if 100 g of fibers having a coating of silver on 100% of the fiber surface are used to remove the mercury from 1000 kg of a mercury-containing solution, it would require 1000 g of fibers having a coating of silver on 10% of the fiber surface to remove the same amount of mercury from 1000 kg of the same mercury-containing solution.

The wet-chemical deposition of silver layers on glass is known from the production of mirrors. Using conventional mirror coating procedures, such as those disclosed by Böttger-Bothe or Brashear (cf. E.v. Angerer, Techn. Kunstgriffe [Technological Tricks], 8th edition, 1952, p. 94 et. seq.), the fibers can be coated with a silver layer very easily and without risk. These mirror coating procedures use ammoniacal silver salt solutions which, if conventionally prepared, can be stored for days without the formation of precipitates of explosive silver fulminates. As noted above, activated carbons impregnated with silver are known to be liable to explosive decomposition. This risk, however, does not apply to the fibers coated with a silver layer, since the fibers used according to the invention do not have an internal, active surface with a porous structure.

The silver coated fibers of the present invention can be prepared prior to packing in the column or directly within the packed column. If the above-mentioned silvering procedures are used, it is not necessary to coat the fibers with a silver layer in a separate process step prior to packing the fibers within the column. For example, the fibers can be coated with a silver layer directly within the packed column by packing the fibers in the column and filling the column with a solution of an ammoniacal silver salt and a reducing agent, such as Seignette salt, in accordance with Böttger-Bothe for a period of several hours, preferably 3–10 hours, most preferably 4–7 hours. The column is then rinsed with water or another suitable solvent, such as methanol or ethanol, to give a column containing silver-coated fiber packing which is ready for use.

Preferably, the packing density of the fibers coated with a silver layer should be, depending on the specific weight of the fiber material, from 0.05 to 0.5 g/cm$^3$. The amount of silver contained in the silver coated fiber is from 0.5 to 10% by weight based on the total weight of the silver-coated fiber, preferably 0.5 to 7.5% by weight.

Compared to column packings using granular or powdered materials, the silver-coated fibers of the present invention have a very small resistance to flowing liquids, similar to conventional uncoated filter materials and loose felts. This is due to the favorable ratio of fiber volume to free volume, which is related to the low packing density.

The silver-coated fiber packings of the present invention also have the advantage of ease of disposal since the exhausted column packings of the present invention can be highly compressed, in contrast to the granular beds of the conventional processes. This ability to undergo high compaction is especially important in the case of safe disposal in an expensive subterranean dump. Moreover, if the fibers used in the present invention are based on a heat-resistant material, such as, for example, rock wool, glass wool or carbon wool, it is also possible to vaporize the mercury out of the fiber in accordance with procedures disclosed in U.S. Pat. No. 4,230,486.

An additional advantage of the fibers used according to the invention, in contrast to using activated carbon, is the fact that the fibers used according to the invention can be very easily rinsed and subsequently rapidly dried. Both after the coating of the fibers with a silver layer and after exhaustion of the column packing prior to its safe disposal, thorough rinsing procedures have to be carried out.

After eliminating mercury from the mercury containing liquid by the method of the present invention, the residual mercury in the treated liquid is preferably <200 ppb, most preferably <5 ppb based on the weight of the liquid.

Having generally described this invention, a further understanding can be obtained by reference to certain specific examples which are provided herein for purposes of illustration only and are not intended to be limiting unless otherwise specified.

EXAMPLE 1

A vertical glass tube having an internal diameter of 2.7 cm and a heatable jacket was filled with 31 g of pearled rock wool (pearl wool available from Isola-Mineralwolle- Werke, D-4322 Sprockhövel 2) having a mean fiber diameter of 10 $\mu$m. The packing height was approximately 16 cm, corresponding to a volume of approximately 90 cm$^3$. This packed column was filled at room temperature with about 100 ml of ammoniacal silver salt/Seignette salt solution as a mirroring solution according to Böttger-Bothe. After approximately 5 hours, the pearl wool, coated with a silver layer of approximately 0.4 g of Ag, was rinsed in the column with water and subsequently with methanol. The column was then heated to a temperature of 60° to 80° C. and charged with a solution of 30% by weight of sodium methylate in methanol. The sodium methylate solution passed through the column from top to bottom with an intrinsic hydrostatic pressure of approximately 30 cm of liquid column. At the bottom part of the column, approximately 350 g/h of sodium methylate solution were taken off continuously. Although the mercury content of the sodium methylate solution being added fluctuated between 220 and 1500 ppb by weight (average content: approximately 600 ppb by weight), the mercury content of the effluent solution was always<5 ppb by weight, up to an off-take of 162 kg of sodium methylate solution. By the time a total off-take of 197 kg of sodium methylate solution had been reached, the mercury content of the solution had risen to 110 ppb by weight indicating the approach of saturation of the mercury removal capability.

EXAMPLE 2

The same test apparatus as in Example 1 was packed with 5 g of polypropylene wool available from Faserwerke Bottrop (Hüls AG) having a fiber diameter of 21 μm. Prior to this, the polypropylene wool was separately coated with a silver layer according to the same procedure as described in Example 1, and was washed and dried. The column packing height and packing volume, and the amount of silver, were identical with Example 1. Using a continuous throughput of approximately 300 g/h of sodium methylate solution according to Example 1, the mercury content of the solution stayed at<5 ppb by weight up to an off-take of 181 kg of sodium methylate solution.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the U.S. is:

1. A method for eliminating mercury from a mercury-containing liquid, comprising:
   contacting the mercury-containing liquid with a plurality of fibers having a coating of silver, wherein said plurality of fibers is made of fibers having diameters of from 5 to 500 μm, by passing the mercury-containing liquid through a mass formed of said silver coated fibers.

2. The method according to claim 1, wherein said plurality of fibers is made of a fiber selected from the group consisting of rock wool, slag wool, glass wool, carbon fibers and plastic fibers.

3. The method according to claim 1, wherein said plurality of fibers is made of fibers having diameters of from 10 to 30 μm.

4. The method according to claim 1, wherein said mercury-containing liquid comprises mercury in a solution of aqueous alkali metal hydroxides or alkali metal alcoholate.

5. The method according to claim 1, wherein said coating of silver is on at least 10% of the surface of said fibers.

6. The method according to claim 1, wherein said coating of silver is on at least 75% of the surface of said fibers.

7. The method according to claim 1, wherein said coating of silver is on 100% of the surface of said fibers.

8. A method for eliminating mercury from a mercury-containing liquid, comprising:
   packing a tube with a plurality of fibers to give a fiber-packed tube;
   filling said fiber-packed tube with a solution comprising an ammoniacal silver salt and a reducing agent to obtain a plurality of fibers having a coating of silver in said tube; and
   contacting said mercury-containing liquid with said plurality of silver-coated fibers packed in said tube by passing the mercury-containing liquid through the packed tube.

9. The method according to claim 8, wherein said plurality of fibers is made of a fiber selected from the group consisting of rock wool, slag wool, glass wool, carbon fibers and plastic fibers.

10. The method according to claim 8, wherein said plurality of fibers is made of fibers having diameters of from 5 to 500 μm.

11. The method according to claim 10, wherein said plurality of fibers is made of fibers having diameters of from 10 to 30 μm.

12. The method according to claim 8, wherein said mercury-containing liquid comprises mercury in a solution of aqueous alkali metal hydroxides or alkali metal alcoholate.

13. The method according to claim 8, wherein said coating of silver is on at least 10% of the surface of said fibers.

14. The method according to claim 8, wherein said coating of silver is on at least 75% of the surface of said fibers.

15. The method according to claim 8, wherein said coating of silver is on 100% of the surface of said fibers.

* * * * *